United States Patent
Heindl et al.

(10) Patent No.: US 7,741,472 B2
(45) Date of Patent: Jun. 22, 2010

(54) POLYNUCLEOTIDE CONTAINING A PHOSPHATE MIMETIC

(75) Inventors: Dieter Heindl, Paehl (DE); Dirk Kessler, Peiting (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 245 days.

(21) Appl. No.: 12/121,842

(22) Filed: May 16, 2008

(65) Prior Publication Data

US 2009/0005550 A1      Jan. 1, 2009

Related U.S. Application Data

(63) Continuation of application No. PCT/EP2006/008842, filed on Sep. 1, 2006.

(30) Foreign Application Priority Data

Nov. 23, 2005   (EP)   ................... 05025499

(51) Int. Cl.
    C07H 21/00   (2006.01)
(52) U.S. Cl. .................... 536/25.3; 536/22.1; 536/24.3; 536/25.33; 536/25.34
(58) Field of Classification Search ........................ None
    See application file for complete search history.

(56) References Cited

U.S. PATENT DOCUMENTS

| | | | |
|---|---|---|---|
| 4,997,928 | A | 3/1991 | Hobbs, Jr. |
| 5,002,885 | A | 3/1991 | Stavrianopoulos |
| 5,118,801 | A | 6/1992 | Lizardi et al. |
| 5,210,015 | A | 5/1993 | Gelfand et al. |
| 5,231,191 | A | 7/1993 | Woo et al. |
| 5,241,060 | A | 8/1993 | Engelhardt et al. |
| 5,260,433 | A | 11/1993 | Engelhardt et al. |
| 5,290,925 | A | 3/1994 | Fino |
| 5,401,837 | A | 3/1995 | Nelson |
| 5,487,972 | A | 1/1996 | Gelfand et al. |
| 5,538,848 | A | 7/1996 | Livak et al. |
| 5,624,711 | A | 4/1997 | Sundberg et al. |
| 5,656,744 | A | 8/1997 | Arnold, Jr. et al. |
| 5,668,266 | A | 9/1997 | Ruth |
| 5,804,375 | A | 9/1998 | Gelfand et al. |
| 6,130,323 | A | 10/2000 | Su et al. |

FOREIGN PATENT DOCUMENTS

| | | |
|---|---|---|
| DE | 19650252 C2 | 6/1998 |
| EP | 1155027 B1 | 11/2001 |
| WO | 9108213 A1 | 6/1991 |
| WO | 9746707 A2 | 12/1997 |
| WO | 0114401 A1 | 3/2001 |
| WO | 0214555 A2 | 2/2002 |
| WO | 03002587 A2 | 1/2003 |
| WO | 2007059816 A1 | 5/2007 |

OTHER PUBLICATIONS

Agrawal, S., "Functionalization of Oligonucleotides with Amino Groups and Attachment of Amino Specific Reporter Groups", Methods in Molecular Biology, vol. 26: Protocol for Oligonucleotide Conjugates, 1994, p. 93-120.

Baschang, G., Kvita, V., Angewandte Chemie (85(1) 19783, 43-44.

Beaucage, S., "Oligodeoxyribonucleotides Synthesis", Methods in Molecular Biology, vol. 20: Protocols for Oligonucleotides and Analogs, 1993, pp. 33-61.

Bernard. P., M., Wittwer, C., "Integrated Amplification and Detection of the C677T Point Mutation in the Methylenetetrahydrofolate Reductase Gene by Fluorescence Resonance Energy Transfer and Probe Melting Curves", Analytical Biochemistry 255 (1998), 101-107.

Brase, S., Gil, C., Knepper, K., Zimmermann, V., "Organische Azide—explodierende Vielfalt bei einer einzigartigen Substanzklasse", Angewandte Chemie 117 (2005) 5320-5374.

Bergers, P., Eckstein, F., "Diastereomers of 5'O'Adenosyl 3'-O-Uridyl Phosphorothioate: Chemical Synthesis and Enzymatic Properties", Biochemistry, 1979, 592-596.

Bustin, S., A-Z of Quantitative PCR, ed. by Stephen A. Bustin, Chapters 6 and 10 (2004), 215-278 and 384-438.

Ghosh, P., Kumar, P., Gupta, K., "Advances in Functionalization of Polymer supports for Synthesis and Modification of Oligonucleotides", J. Indian Chem. Soc. vol. 75, Apr. 1998, pp. 206-218.

"DCI—A Logical Alternative Activator", Glen Research Report No. 10 (GR10-1) 1997, 1-12.

Greene, T., "Protective Groups in Organic Synthesis", John Wiley & Sons, 1981 New York, Chichester, Brisbane Toronto.

(Continued)

*Primary Examiner*—Patrick T Lewis
(74) *Attorney, Agent, or Firm*—Marilyn Amick; Roche Diagnostics Operatios, Inc.

(57) ABSTRACT

The present invention concerns modified oligonucleotides and processes for their production wherein these oligonucleotides contain at least once the structure P═N-Acc where Acc is an electron acceptor or an electron acceptor substituted with a residue R and R is any organic substituent.

7 Claims, No Drawings

OTHER PUBLICATIONS

Hansch, C., Leo, A., Taft, R., "A Survey of Hammett substituent Constant and Resonance and Field Parameters", Chem Reviews 91 (1991) 165-195.

Hodges, R., Conway, N., McLaughlin, L., "Post-Assay Covalent Labeling of Phosphorothioate-Containing Nucleic Acids with Multiple Fluoroscent Markers", Biochemistry 1989, 28, 261-267.

Jung, P.M. et al., "Parallel solid-Phase Synthesis of Nucleoside Phosphoramidate Libraries", Bioorganic & Medicinal Chemistry Letters 11 (2001) 2057-2060.

Matthews, J., Kricka, J., "Analytical Strategies for the Use of DNA Probes", Analytical Biochemistry 169, 1-25 (1988).

McMurry, J., Coppolino, A., "The Cyanogen Azide Ring-Expansion Reaction", J. Org. Chem., vol. 38, No. 16, 1973, 2821-2827.

Miller, P., Yano, J., Yano, E., Carroll, C., Jayaraman, K., Ts'o, P., "Nonionic Nucleic Acid Analogues. Synthesis and Characterization of Dideoxyribonucleoside Methylphosphonates", Biochemistry 18 (1979) 5134-5143.

Nielsen, J., Caruthers, M., "Directed Arbuzov-Type Reactions of 2-Cyano-1, 1-dimethylethyl Deoxynucleoside Phosphites", J. Am. Chem. Soc. 1988, 110, 6275-6276.

Selinger, H., Hinz, M., Happ, E., "Arrays of Immobilized Oligonucleotides—Contributions to Nucleic Acids Technology", Current Pharmaceutical Biotechnology 2003, 4, 379-395.

Shoepinov, M., Case-Green, S., Southern, E., "Steric factors influencing hybridisation of nucleic acids to oligonucleotide arrays", Nucleic Acids Research, 1997, vol. 25, No. 6, 1155-1161.

Wojczewski, C., Stolze, K., Engels, J., "Fluorescent Oligonucleotides—Versatile Tools as Probes and Primers for DNA and RNA Analysis", Synlett 1999, No. 10, 1667-1678.

POLYNUCLEOTIDE CONTAINING A PHOSPHATE MIMETIC

RELATED APPLICATIONS

This application is a continuation of PCT/EP2006/008842 filed Sep. 1, 2006 and claims priority to EP 05025499.4 filed Nov. 23, 2005.

FIELD OF THE INVENTION

The present invention concerns new substances and processes, for producing them in the field of nucleotide chemistry. These substances are so-called phosphate mimetics in which a hydroxyl group is replaced by a corresponding mimetic. In particular the present invention concerns a new class of modified oligonucleotides and processes for their production.

BACKGROUND

Various processes have already been previously described to produce nucleotides or oligonucleotides with a modified phosphate residue. Synthetic (deoxy) oligonucleotides are usually prepared on a solid phase with the aid of phosphoramidite chemistry. Glass beads with pores of a defined size are usually used as the solid phase (abbreviated in the following as CPG=controlled pore glass). The first monomer is linked to the support by a cleavable group so that the free oligonucleotide can be cleaved off after completion of the solid phase synthesis. In addition the first monomer contains a protected hydroxyl group in which case dimethoxytrityl (DMT) is usually used as the protective group. The protective group can be removed by acid treatment. Then at the 5' end, 3' phosphoramidite derivatives of (deoxy) ribonucleosides that are also provided with a DMT protective group are successively coupled to the reactive group that is freed in each case of the DMT protective group in a cyclic process. Alternatively 3' dimethoxytrityl-protected 5' phosphoramidites are used in inverse oligonucleotide synthesis. The H-phosphonate strategy is also used in particular to introduce modifications on the phosphate backbone, e.g., to prepare radiolabeled phosphorothioates. Various strategies are also already known for preparing modified or labeled oligonucleotides: trifunctional support materials are used according to the prior art to prepared oligonucleotides labeled at the 3' end (U.S. Pat. No. 5,290,925, U.S. Pat. No. 5,401,837). Labeled phosphoramidites in which the labeling group is bound to the phosphoramidite via a C3-12 linker are usually used to prepare oligonucleotides labeled at the 5' end (U.S. Pat. No. 4,997,928, U.S. Pat. No. 5,231,191). Furthermore modifications can be introduced into oligonucleotides on the individual bases (U.S. Pat. No. 5,241,060, U.S. Pat. No. 5,260,433, U.S. Pat. No. 5,668,266) or by introducing internal non-nucleoside linkers (U.S. Pat. No. 5,656,744, U.S. Pat. No. 6,130,323).

Alternatively an internucleoside phosphate can be labeled by postsynthetic labeling of phosphorothioates (Hodges, R. R., et al. Biochemistry 28 (1989) 261-7) or by post-labeling a functionalized phosphoramidite (Agrawal, S., Methods in Mol. Biology 26 (1993), Protocols for Oligonucleotide Conjugates, Humana Press, Totowa; NJ, Chapter 3). However, these methods have not gained acceptance due to the instability of the phosphoramidites and phosphoric acid thioesters.

It is also already known from the prior art that modifications can be introduced on the inter-nucleoside phosphate residue of oligonucleotides. In the most prominent cases these are phosphothioates (Burgers, P. M., and Eckstein, F., Biochemistry 18, (1979) 592-6), methylphosphonates (Miller, P. S., et al., Biochemistry 18 (1979) 5134-43) or boranophosphates (WO 91/08213). Special monomers have to be synthesized in order to prepare methylphosphonate oligonucleotides. In contrast conventional phosphoramidites or H-phosphonates can be used to synthesize phosphorothioates and boranophosphates in which case the borano or thio modification can be introduced directly during or also after oligonucleotide synthesis by using special reagents that react with the trivalent H-phosphonate or with the phosphonic acid triester. Although all these methods lead to modified oligonucleotides, the requirements of the synthesis chemistry used for this does not allow labels that can be detected in this manner or functional groups to be directly introduced on the phosphate backbone of the oligonucleotide chain during oligonucleotide synthesis.

Baschang, G., and Kvita, V., Angewandte Chemie 85(1) (1973) 43-44 describe the reaction of a nucleotide phosphoric acid triester with azides such as methylsulfonyl azide to prepare trialkyl(aryl)imidophosphates which are, however, unstable and decompose.

Nielsen, J., and Caruthers, M. H., J. Am. Chem. Soc. 110 (1988) 6275-6276 describe the reaction of deoxynucleoside phosphites provided with a 2-cyano-1,1-dimethylethyl protective group in the presence of alkyl azide. Furthermore, the authors suggest that this principle is suitable for preparing nucleotides that are modified on the phosphate residue without elucidating which types of modifications prepared with the aid of the disclosed method could have particular advantages. In particular the authors suggest the introduction of alkyl residues.

WO 89/091221 discloses N-alkyl phosphoramidites or rather oligonucleotides substituted with N-alkyl on at least one phosphate residue which are prepared by oxidizing nucleoside phosphites (provided with a protective group) with iodine in the presence of suitable alkylamines.

WO 03/02587 discloses the preparation of modified oligonucleotides in which H-phosphates are converted by amination into phosphoramidates.

Thus all of these publications describe the preparation of molecules which contain a phosphoramidate instead of a phosphate residue. However, molecules containing phosphoramidate are susceptible to hydrolysis since the anine group is protonated in an acidic environment and is then substituted by water.

In addition WO 01/1.4401 proposes nucleotide building blocks or oligonucleotides in which a phosphate residue is substituted with N—ClO$_3$, N—NO$_2$ or N—SO$_2$R. According to the teaching, from WO 01/14401 such substances can be prepared by reacting the free hydroxyl group of a deoxy nucleoside with amidophosphonyl chloride in the presence of pyridine. However, this type of preparation is complicated, time-consuming and unsuitable for the routine synthesis of nucleotides or oligonucleotides.

The technical object forming the basis of the present invention was thus to prepare improved labeled to oligonucleotides and to provide a simple process for their preparation.

SUMMARY OF THE INVENTION

Hence the present invention concerns a chemical compound, which is preferably an oligonucleotide containing at least once the structure

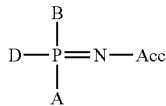

in which A represents the 5' end of a nucleotide or a nucleotide chain or it represents a linker bound to a solid phase, B represents the 3' end of a nucleotide or a nucleotide chain or it represents a linker, D is either OH or CH$_3$, and Acc is an electron acceptor or an electron acceptor substituted with a residue R and R is any organic substituent.

The electron acceptor Acc is preferably selected from a group comprising —CN, —SO$_2$—R', in which R' contains at least one amino-substituted alkyl, an optionally substituted aryl or an optionally substituted heterocycle, and electron-deficient, six-membered N$^+$-heterocycles in which at least one nitrogen atom is alkylated and is located in the ortho or para position and wherein these heterocycles can be optionally substituted with R.

Oligonucleotides are particularly preferred in which R or R' alone or in combination with the electron acceptor contain a detectable unit or a functional group.

These oligonucleotides are prepared according to the invention by processes which are characterized in that a trivalent phosphorus derivative of the chemical structure

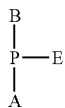

in which E either represents a methyl group or a protected hydroxyl group, A represents the 5' end of a nucleotide or of a nucleotide chain or represents a linker bound to a solid phase, and B represents the 3' end of a nucleotide or of a nucleotide chain or represents a linker, is reacted with an azide of the structure

in which Acc is an electron acceptor or an electron acceptor substituted with a residue R and R is any organic substituent.

The electron acceptor Acc is preferably selected from the group comprising —CN, —SO$_2$—R, and electron-deficient, six-membered N$^+$-heterocycles in which at least one nitrogen atom is alkylated and is located in the ortho or para position and wherein these heterocycles can be optionally substituted with R.

In a special embodiment for producing an oligonucleotide according to the invention,
a) a 3' phosphoramidite is firstly reacted with the 5' OH end of a nascent oligonucleotide chain, and subsequently
b) reaction of an azide of the structure

in which Acc is an electron acceptor or an electron acceptor substituted with the residue R and R is any organic substituent.

Processes are particularly preferred in which R contains a detectable unit or a functional group.

Oligonucleotides according to the invention that are produced in this manner can be used for all applications in which hybridization partners in any form and in particular derivatized or labeled hybridization partners are required.

In particular these oligonucleotides can be used as hybridization probes for detecting certain target sequences.

Another potential use concerns the use of oligonucleotides modified according to the invention for inactivating gene expression in the form of antisense oligonucleotides or siRNAs.

DETAILED DESCRIPTION OF THE INVENTION

The object of the present invention is to produce nucleotides and oligonucleotides in a simple manner which contain modified phosphate residues and thus can also preferably contain detectable labels.

The central idea of the present invention was in this connection to start with a trivalent phosphorus atom and to react it with a reagent in such a manner that a stable phosphate mimetic is formed. According to the invention a phosphorus atom containing at least one hydroxyl residue which is provided with a protective group is for this purpose reacted with an azide having the structure N═N═N-Acc in which Acc is an electron acceptor or an electron acceptor substituted with a residue R and R is any organic substituent. This results in the formation of a pentavalent phosphorus atom to which a strongly electron-attracting electron acceptor group is covalently bound via an N atom. This group ensures that the compounds produced in this manner are, in contrast to the phosphoramidate compounds known from the prior art, resonance-stabilized and are not susceptible to hydrolysis.

This idea underlying the invention can be applied to all processes in which a trivalent phosphorus is formed as an intermediate.

During conventional oligonucleotide synthesis using phosphoramidites, phosphonic acid triesters with a trivalent phosphorus atom are formed as intermediate products. The first, and second ester bond represent the internucleoside linkage. The phosphorus atom is linked to a protected hydroxyl group such as for example to a beta-cyanoethyloxy group via the third ester bond. Instead of an oxidation with iodine, the nascent oligonucleotide can then be reacted according to the invention with an appropriate azide in the process of which the trivalent phosphorus atom is oxidized to a pentavalent atom by covalently linking —N-Acc to the phosphorus atom while cleaving nitrogen.

Oligonucleotide synthesis can then be subsequently continued as known from the prior art. Stable oligonucleotides are obtained as an end product which are modified in almost any manner on one or more internucleotide phosphate residues.

Within the scope of the present invention some of the terms used are defined as follows:

Reactive group refers to groups of a molecule which are able to react under suitable conditions with another molecule while forming a covalent bond. Examples of reactive groups are hydroxyl groups, amino groups, thiol, hydrazino, hydroxylamino, diene, alkine and carboxylic acid groups.

Protective group denotes molecules which react with one or more reactive groups of a molecule such that, as part of a multistep synthesis reaction, only one particular, non-protected reactive group can react with the desired reaction partner. Examples of frequently used protective groups to protect hydroxyl groups are beta-cyano-ethyl, trialkylsilyl and allyl. Protective groups for protecting amino groups are trifluoroacetyl and Fmoc. Other possible protective groups are summarized in standard text books (Greene, T. W., Protective groups in organic synthesis. Wiley Interscience Publications John Wiley&Sons (1981) New York, Chichester, Brisbane, Toronto; Souveaux, E., Methods in Mol. Biology, Vol. 26, Protocols for Oligonucleotide Conjugates, Humana Press, Totowa, N.J., 1994, Chapter 1, ed. S. Agrawal).

Linkers denotes carbon chains having a length of 1-30 C atoms. Such linker chains can also additionally have one or more internal nitrogen, oxygen, sulphur and/or phosphorus atoms. Linkers can also be branched, e.g., also be dendritic. Linker interconnect a nucleotide or a chain of nucleotides with either a detectable unit or a reactive group which is optionally protected by a protective group.

A detectable unit is understood to denote substances which can be detected with the aid of analytical methods. They can for example be units that can be detected by mass spectroscopy, immunologically or with the aid of NMR. Detectable units are in particular also substances that can be detected by optical methods such as fluorescence and UV/VIS spectroscopy such as fluoresceins, rhodamines and gold particles. They also include intercalators and minor groove binders which can also have an effect on the melting behaviour and whose fluorescence is changed by hybridization.

Phosphoramidites denote molecules containing a trivalent phosphorus atom which can be coupled to the 5' terminal end of a nucleoside or nucleoside derivative. Thus phosphoramidites can be used in oligonucleotide synthesis. In addition to (deoxy)ribonucleotide-phosphoramidites that are used for chain extension, there are also phosphoramidites derivatized with a label which can be used in similar processes during or at the end of oligonucleotide synthesis to label the oligonucleotide (Beaucage, S. L., Methods in Molecular Biology 20 (1993) 33-61, ed. S. Agrawal; Wojczewski, C., et al., Synlett 10 (1999) 1667-1678).

In connection with the present invention the term "oligonucleotides" encompasses not only (deoxy) oligoribonucleotides but also oligonucleotides which contain one or more nucleotide analogues with modifications on the phosphate backbone (such as for example methyl phosphonates, phosphothioates), on the sugar (such as 2'-O-alkyl derivatives, 3' and/or 5' amino ribose, LNA, HNA, TCA) or modified bases such as 7-deazapurine. In thus connection the invention also encompasses conjugates and chimeras containing non-nucleosidic analogues such as PNAs or other biopolymers, e.g., peptides. Furthermore, the oligonucleotides according to the invention can also contain one or more non-nucleosidic units such as spacers at each position, e.g., hexaethylene glycol or Cn (n=3.6) spacers.

The term "electron acceptor" encompasses atomic structures which have the tendency to bind free electron pairs. One measure of this is the Hammett constant. The present invention concerns in particular embodiments in which the Hammett constant $\sigma_p$ exceeds a certain value of 0.30, preferably 0.45 and particularly preferably 0.60.

The electron acceptor must additionally be compatible with all chemical reactions in oligonucleotide synthesis, i.e., it should not be oxidized by iodine, it must be inert towards dichloroacetic acid and trichloroacetic acid, it must be inert towards bases and in particular towards ammonia, and it should not react with trivalent phosphoramidites.

Examples of electron acceptors which fulfil these conditions include —$NO_2$, $SO_2$—R, —CN, —CO—R, pyrimidinyl, pyridinyl, pyridazinyl, hexafluorophenyl, benzotriazolyl (Hansch, C., et al., Chem. Reviews 91 (1991) 165-195). In addition these acceptors can also be bound to the nitrogen atom in a vinylogous or phenylogous manner.

The term "substituted" means that the structure that is referred to as being substituted contains another residue at any position provided this position is not defined in more detail. The term "optionally substituted" denotes that the structure referred to in this manner comprises embodiments with and without an additional residue.

The term "amino-substituted alkyl" encompasses $C_1$-$C_{30}$ linear or branched alkyl which contains at least one amino group where this amino group is protected or is bound to a detectable unit via a linker.

The term "six-membered N⁺-heterocycle" encompasses N-heterocycles, which are alkylated on an sp2 nitrogen such that the overall charge of the heterocycle is positive. Examples of this are pyridinium, pyrimidinium and quinolinium. Such heterocycles are known in the art to be electron deficient.

The term "nucleotide chain" is understood as a molecule or a part of a molecule containing at least two nucleoside residues which are 5'-3' inter-connected by a phosphate moiety.

The present invention encompasses any chemical compound containing at least once the structure

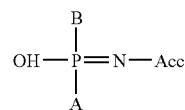

in which A represents the 5' end of a nucleotide or of a nucleotide chain or it represents a linker bound to a solid phase and B represents the 3' end of a nucleotide or of a nucleotide chain or it represents a linker and Acc is an electron acceptor or an electron acceptor substituted with a residue R and R is any organic substituent. This residue must be additionally compatible with all chemical reactions occurring in oligonucleotide synthesis, i.e., it should not be oxidized by iodine, it must be inert towards dichloroacetic acid and trichloroacetic acid, it must be inert towards bases and in particular towards ammonia, and it should not react with trivalent phosphoramidates.

Residues that are initially per se incompatible can, however, be converted, into derivatives which behave inertly under the chemical conditions of oligonucleotide synthesis by using protective groups known to a person skilled in the art.

It is also understood by a person skilled in the art that the —OH groups of the oligonucleotide are usually present, in a deprotonated status.

Moreover the present invention also encompasses methyl phosphonates of the structure

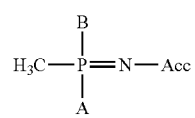

with the definitions given above.

In a first, preferred embodiment, the chemical compound of the present invention is an Oligonucleotide. In such an oligonucleotide, A represents the 5' end of a nucleotide or of a nucleotide chain and/or B represents the 3' end of a nucleotide or a nucleotide chain. Thus, A and B together comprise at least two nucleotide residues.

Depending on the intended use of the oligonucleotide, the structures described above can occur once, twice, many frames or even on all phosphate residues present in the oligonucleotide. The phosphate residues within the oligonucleotide are so-called internucleoside phosphates such that A represents the 5' end of a first nucleoside and B represents the 3' end of a second nucleoside within the nucleotide chain.

Furthermore the structures according to the invention can be located at the 3' end or 5' end of an oligonucleotide. If they are present at the 5' end of the oligonucleotide, then A represents the 5' end of the nucleotide chain and B is either an optionally protected hydroxyl group or a linker which can optionally contain a detectable group or another reactive group, and can be used to introduce a detectable group on the oligonucleotide.

If the electron acceptor contains a substituent which also represents a detectable unit, an oligonucleotide is present according to the invention may carry a dual label at the 5' end.

If the structure according to the invention is at the 3' end of a nucleotide chain, then B represents the 3' end of the said oligonucleotide and A is either hydroxyl or a linker bound to a solid phase wherein the solid phase is preferably controlled pore glass particles such as those that are used as a starting material for routine oligonucleotide synthesis.

The individual nucleosides within the oligonucleotides according to the invention can contain any type of nucleosides or modified nucleosides or nucleoside derivatives. The sugar units are usually deoxyribose for DNA oligonucleotides or ribose for RNA oligonucleotides. The nucleobases contained in the oligonucleotides according to the invention can be naturally occurring bases such as adenine, guanine, thymidine, cytidine, uridine, derivatives thereof or so-called universal bases such as, nitroindole. The oligonucleotides according to the invention can contain any electron acceptor groups which are linked via an amide bond to the respective phosphate. In particular the following electron acceptor groups can be used: —CN, —SO$_2$—R', in which R' contains at least one amino-substituted alkyl, an optionally substituted aryl or an optionally substituted heterocycle, and electron-deficient, six-membered N$^+$-heterocycles in which at least one nitrogen atom is alkylated and is located in the ortho or para position and wherein these heterocycles can be optionally substituted with R.

The invention unequivocally also encompasses embodiments of SO$_2$—R' in which R' as such is an amino-substituted alkyl, an optionally substituted aryl, or an optionally substituted heterocycle.

The presence of all said electron acceptors within the oligonucleotides according to the invention results in modified oligonucleotides which can be used for a wide variety of applications. However, all electron acceptors which can contain any organic residue R are of particular interest because they allow modified oligonucleotides containing any organic residues to be prepared in a simple manner within the scope of the synthesis processes described in this application.

Hence the present invention concerns in particular also oligonucleotides in which an electron acceptor substituted with a residue R contains a detectable unit as R or alternatively contains a functional group as R to which a detectable unit can be coupled after the oligonucleotide synthesis by post-labeling. Alternatively the present invention also encompasses embodiments in which the electron acceptor is a component of the detectable unit. Alternatively the residue R can itself be the detectable unit or functional group.

Such labeled oligonucleotides can be used advantageously for numerous different applications in molecular biology such as in real time PCR. The detectable label is preferably a fluorescent dye or a fluorescence quencher molecule. Corresponding dyes and molecules which can serve as a detectable unit for oligonucleotides are well known to a person skilled in the art. Examples of these that do not limit the protective scope of the present invention are: fluoresceins, rhodamines cyanines, merocyanines, carbocyanines and azo and poly-azo compounds.

The present invention also concerns real time PCR probes having the structure described above in which at least one fluorescent label is bound to the phosphate atom of the oligonucletide chain by means of an amide/electron acceptor group. Examples of such probes are FRET hybridization probes (WO 97/46707) or so-called single-labeled probes (WO 02/14555). In this connection oligonucleotide probes in which there is an internal modification according to the invention on an internucleoside phosphate residue are particularly preferred.

In this connection the present invention also particularly concerns dual labeled oligonucleotides which have two detectable units. Examples of such probes are TaqMan probes (U.S. Pat. No. 5,804,375) molecular beacons (U.S. Pat. No. 5,118,801). In this connection the present invention concerns dual labeled oligonucleotides in which a first fluorescent label is bound to an internucleoside phosphate atom of the oligonucleotide chain by means of an amide/electron acceptor group and a second detectable unit is present terminally at the 5' end or 3' end of the oligonucleotide. Molecules which have such labels and methods for their preparation are well-known among experts.

In a further aspect, the present invention is directed to a chemical compound having the structure

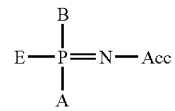

in which A represents a linker bound to a solid phase, B represents a linker which preferably carries a protected reactive group or a detectable unit, E is either methyl or a protected hydroxyl, and Acc is an electron acceptor or an electron acceptor substituted with a residue R and R is any organic substituent.

With respect to B, the preferred protected reactive group is a dimethoxytrityl (DMT) protected hydroxyl group. With respect to E, the preferred protecting group is a beta-cyanoethyl group.

Such a compound may be used as a starting material for oligonucleotide synthesis, wherein the next Phosphoramidate is reacting with the remaining hydroxyl group of said compound. Furthermore, in a case A represents a trifunctional linker with an extra arm, it is possible to produce an oligonucleotide with dual label at its 3' end, characterized in that one label is introduced via the Acc substituent and the second label is introduced via a further moiety connected to the linker.

The present invention also concerns processes for producing modified oligonucleotides and in particular processes for producing the oligonucleotides that were described above.

In general the present invention concerns processes for producing modified oligonucleotides which are characterized in that a trivalent phosphorus derivative of the chemical structure

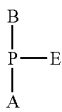

in which E is either a methyl group or a protected hydroxyl, which is preferably protected by a beta-cyanoethyl group, A represents the 5' end of a nucleotide or of a nucleotide chain or it represents a linker bound to a solid phase, and B represents the 3' end of a nucleotide or of a nucleotide chain or it represents a linker, is reacted with an azide of the following structure

in which Acc is an electron acceptor or an electron acceptor substituted with a residue R and R is any organic substituent.

Beta-cyanoethyl, methyl, allyl or silyl are particularly preferred as protective groups. Alternatively methyl-phosphonates can be produced according to the invention in which E is $CH_3$.

According to the invention the azides can contain any electron acceptor groups. These groups are then linked with the respective phosphorus atom. In particular the following electron acceptor groups can be used: —CN, —$SO_2$—R, and electron-deficient, six-membered $N^+$-heterocycles in which at least one nitrogen atom is alkylated and is located in the ortho or para position and wherein these heterocycles can be optionally substituted with R.

The process according to the invention can also be routinely used, in particular within a conventional oligonucleotide synthesis. Hence the present invention also concerns a process comprising the steps a) reaction of a 3' phosphoramidite with the 5' OH end of a nascent oligonucleotide chain, and b) reaction with an azide of the structure

in which Acc is an electron acceptor or an electron acceptor substituted with a residue R and R is any organic substituent.

In this case the 5' OH end of the nascent oligonucleotide chain can either be the 5' end of a 5' terminal nucleotide or the free OH group of a linker attached to a CPG.

Conventional oligonucleotide chemistry begins on a reactive solid phase support material. Solid phase support material refers to polymeric substances which form a solid phase containing a reactive group on which further molecules can be immobilized. In the case of oligonucleotide synthesis, the support material is usually porous glass beads with a defined pore size, so-called controlled, pore glass particles (CPG). Alternatively it is also possible to use polystyrene residues and other organic polymers and copolymers (Ghosh, P. K., et al., J. Indian. Chem. Soc. 75 (1998) 206-218). If the oligonucleotides should remain immobilized after the synthesis on the substrate, glass and also semiconductor chips can be used as the solid phase support material. Such solid phase support materials are commercially available.

The support can be bound by means of a so-called linker group containing a cleavable bond to the terminal reactive hydroxyl residue protected by a protective group such as DMT (dimethoxytrityl). A linker group with a cleavable bond denotes those groups which are between the trifunctional spacer and the solid phase support material and can be cleaved by a simple chemical reaction. They can be succinyl or oxalyl or other tinker groups which contain a cleavable ester bond. Other linker groups are known to a person skilled in the art (Ghosh, P. K., et al., J. Indian. Chem. Soc. 75 (1998) 206-218).

Such linker groups are essential for the use of the support material to synthesize oligonucleotides which are intended to be present in aqueous, solution after completion of the synthesis. If, in contrast, the oligonucleotide should remain on the surface of the support material after the synthesis as for the production of nucleic acid arrays (U.S. Pat. No. 5,624, 711, Shehepinov, M. S., et al., Nucl. Acids. Res. 25 (1997) 1155-1161), a cleavable linker groups is unnecessary but rather a non-cleavable linker group is preferred.

The details of an oligonucleotide synthesis for the incorporation of the structures according to the invention are as follows:

A reactive hydroxyl group on which a chain extension in the 3'-5' direction can occur is formed after removing the DMT protective group by acid treatment. Then 3' phosphoramidite derivatives of (deoxy) ribonucleosides that are also provided with a DMT protective group and additional base protecting groups well known in the art are successively coupled at the 5' end to each reactive group freed of the DMT protective group in the presence of tetrazole. An intermediate containing a trivalent phosphorus atom is formed in this process as an intermediate product which forms an ester bond with each of the nucleosides that are linked together by the reaction and a third ester bond with a protected hydroxyl group which is already present in the phosphoramidite that is used. This protective group which can for example be formed by beta-cyanoethyl, methyl, allyl or silyl is subsequently cleaved with ammonia after completion of the oligonucleotide synthesis in the process of which the base protective groups and the linker to the CPG are also cleaved.

Instead of oxidation with the aid of iodine, the nascent oligonucleotide is reacted according to the invention with an azide of the structure

at the positions at which phosphate mimetics are to be introduced into the nucleotide chain, wherein Acc is an electron acceptor or an electron acceptor substituted with a residue R and R is any organic residue. The described synthesis chemistry allows the incorporation of basically any residues R and in particular the incorporation of any type of fluorescent dyes.

The preparation of Acc azides such as acyl azides and sulfonyl azides is simple and known for a long time (Review: Bräse, S., et al., Angewandte Chemie 117 (2205) 5320-5374, 3.4 and 3.5.2). They are preferably prepared from acyl chlorides or sulfonyl chlorides using sodium azides or from hydrazides using nitrous acid.

Dye sulfonyl azides are for example also used in dyeing processes (e.g., DE 19650252). Cyanogen azide can be simply produced by reacting sodium azide with bromocyanogen in acetonitrile (McMurry, J. E., et al., J. Organic Chemistry 38(16) (1973) 2821-7). Heteroaryl azides can be prepared by nucleophilic substitution of a halogen with azide or from heteroaryl hydrazines. A prerequisite is that the electron-attracting nitrogen is in the para or ortho position relative to the azido group since only then is a resonance-stabilized phosphate mimetic formed. Ortho and para N-alkyl pyridinium azides are particularly suitable in this connection. Some acyl, sulfonyl and pyridyl azides are also commercially available.

The present invention additionally concerns processes as described above in which the residue R is a detectable unit. R is preferably a fluorescent dye or a fluorescence quencher molecule.

Certain embodiments of the present invention concern the preparation of dual labeled oligonucleotide probes in which a label is preferably introduced internally into the oligonucleotide according to the inventive process and another label is introduced into the oligonucleotide preferably at the 5' or 3' end according to a method known from the prior art.

In the case of a 5' label at the 5' position of the ribose of the 5'-terminal nucleotide, the incorporation is carried out by conventional methods using a dye-labeled phosphoramidite it the end of the oligonucleotide synthesis (Beaucage, S. L., Methods in Molecular Biology 20 (1993) 33-61, S. Agrawal Publishers).

Labeling at the 3' end is carried out by using commercially available CPG as a reactive solid phase support which already contains a detectable label in addition to the tritylated hydroxyl group. After cleavage of the DMT protective group standard oligonucleotide synthesis can be started at the hydroxyl group which is now free.

Alternatively methods known from the prior art for post-labeling can be used for an additional 5' or 3' label (U.S. Pat. No. 5,002,885, U.S. Pat. No. 5,401,837).

The invention also concerns intermediates of the synthesis according to the invention which can be prepared before the standard oligonucleotide synthesis. In this case intermediates that are still bound to the solid phase and are not yet deprotected and can contain a basic spacer groups are preferred. CPGs which are familiar, to a person skilled in the art as phosphate CPG are preferably used for the preparation since a 3' phosphorylated oligonucleotide is formed after the oligosynthesis. After detritylation such phosphate CPGs are reacted with a spacer phosphoramidite in the presence of an activator. The trivalent phosphorus intermediate that is formed is then reacted with an Acc azide which contains a detectable unit. These intermediates of synthesis can be stored and used like trifunctional CPGs for universal 3' labeling.

The present invention also concerns the synthesis of phosphoramidites which contain a protected N-Acc group instead of a, for example, beta-cyanoethyl-protected oxygen in order to enable N-Acc-phosphorothioates or bis-N-Acc-phosphate mimetics to be synthesized. Such a synthesis strategy is suitable in individual cases for example to prepare oligonucleotides containing P=N—CN.

A trivalent phosphorus intermediate is also formed during the synthesis of methyl phosphonates which can be reacted with azides. Methyl phosphoramidites are also commercially available.

In an inverse synthesis strategy (EP 1 155 027) which is used for standard oligonucleotides as well as in particular for analogues, e.g., for the synthesis of N3'->P5' oligonucleotides, an intermediate containing a trivalent phosphorus is also formed which can be reacted according to the invention with azides. The corresponding phosphoramidites are commercially available.

The synthesis strategy according to the invention allows the preparation of a wide variety of oligonucleotides modified on the phosphate backbone. The degree of modification, the diversity and the charge of the modifications are determined by the intended use.

For example, the oligonucleotides according to the invention can be used to hybridize with natural DNA and RNA, e.g., for capturing or for detection: Oligonucleotides containing P—N=Acc phosphate mimetics alone or as chimeras with normal phosphates can also be used successfully as primers in amplification reactions.

Such oligonucleotide probes are the basis for various applications, e.g., real time PCR, FISH, Blot techniques, sequencing Jung, P. M., et al., Nucleic Acid Amplification Technologies BioTechniques Books, Div. Eaton Publishing (1997) Editors H. H. Lee, S. A. Morse, O. Olsvik; Bustin, Stephen A. and Nolan, Tania. Chemistries. IUL Biotechnology Series (2004), 5(A-Z of Quantitative PCR), 215-278).

The oligonucleotides, labeled according to the invention are particularly suitable as fluorescent-labeled probes in various real time PCR formats:

Dual labeled probes are usually used for the molecular beacon format (U.S. Pat. No. 5,118,801) and for the TaqMan probe format (U.S. Pat. No. 5,210,015, U.S. Pat. No. 5,538, 848 and U.S. Pat. No. 5,487,972, U.S. Pat. No. 5,804,375) in which a label is preferably introduced internally and a second label is located at the 5' or 3' end of the probe. It is especially, advantageous to internally label the probes using a process according to the invention as part of an oligonucleotide synthesis based on phosphoramidite chemistry. The second detectable unit at the 5' or 3' end of the probe can either be also introduced into the corresponding probe by means of one of the described inventive processes or with the aid of processes known from the prior art.

A 5'-terminally labeled probe and a 3'-terminally labeled probe are usually used, for the FRET hybridization probe format (Matthews, J. A., and Kricka, L. J., Analytical Biochemistry 169 (1988) 1-25), (Bernard, P. S., et al., Analytical Biochemistry 255 (1998) 101-107). In this case it is particularly advantageous to carry out the 5'-labeling of the probe using a process according to the invention as part of an oligonucleotide synthesis based on phosphoramidite chemistry.

The present invention allows functionalized oligonucleotides to be prepared in a simple manner in which the electron acceptor Acc is modified with a residue R which contains a functional group that is appropriately protected for the oligosynthesis. If this residue is an amino or hydroxylamino group, then they can be used to for example prepare oligonucleotide arrays by spotting on epoxy-modified surfaces (Seliger, H., et al., Current Pharmaceutical Biotechnology 4 (2003) 379-395). In contrast thiol groups can be used for immobilization on gold surfaces or gold particles. In this case it is particularly advantageous according to the invention when several thiol groups are introduced in a simple manner in order to obtain a stable binding of a capture probe on the gold surface. If a protected OH group is incorporated as the functional group, then branched or dendritic oligonucleotides can also be prepared.

Such functional groups and in particular amino groups can also be used to prepare labeled oligonucleotides by reacting them with the active ester of a dye after the oligosynthesis. However, it is more advantageous to introduce the detectable unit directly during oligonucleotide synthesis according to the inventive process.

Since the oligonucleotides according to the invention are resistant to nucleases, they are also suitable for use in various cell culture experiments known to experts for inactivating gene expression, i.e., the oligonucleotides according, to the invention are used as antisense oligonucleotides or as a component of siRNA active ingredients. In this case the modifications can be selected such that they facilitate cellular uptake and/or improve binding to the target nucleic acid. Inactivation of expression of a respective target gene can subsequently be monitored by means of Northern Blot analysis, one-step or two-step Real-Time RT-PCR or by means of hybridization onto appropriate microarrays.

Furthermore the oligonucleotides according to the invention can be used as hydrophilic linkers between a detectable unit and a protein or as a label of a defined mass. In addition aptamer substance libraries can be set-up in which case it is possible to introduce various residues R on the phosphate during the synthesis by using different sulfonyl azides and acyl azides or heteroaryl azides. Such libraries can then be tested for their binding to proteins or other biomolecules. An advantage over aptamers known in the prior art is that the process according to the invention allows a large number of different additional modifications to be produced and tested in a simple manner.

The invention is elucidated in more detail by the following examples, publications and the sequence protocol, the protective scope of which is derived from the patent claims. The described methods are to be understood as examples which still describe the object of the invention even after modifications.

The following examples and sequence listing are provided to aid the understanding of the present invention, the true scope of which is set forth in the appended claims. It is understood that modifications can be made in the procedures set forth without departing from the spirit of the invention.

EXAMPLE 1

Synthesis of a Modified dT(P(=NSO2PhNHAc)dT

The dimer synthesis was carried out on a 10 µmol scale on an ABI 394 synthesizer. Commercially available dT CPG support was used as the Solid phase. All chemicals for the standard synthesis were obtained from Glen Research.

The conventional oxidizer solution containing iodine was replaced by a 0.1 M solution of p-NAc phenylsulfonyl azide (Sigma Aldrich) in anhydrous acetonitrile. The oxidation time was extended to 16 min.

The product was cleaved from the support for 2 h at room temperature with 33% ammonia and separated by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant is measured at 260 nm. There was a main fraction which contained the desired product. The solvent was removed on a vacuum centrifuge. The residue was taken up in redistilled water and was again evaporated in a vacuum. This procedure was repeated three times. The residue was then dissolved in redistilled water and lyophilized.

1H NMR: (Bruker DPX 300) in D2O: 7.82 d[2H, aryl], 7.56 d[2H aryl], 7.47 s[1H, C6-H], 7.40-[1H, C6-H], 6.21 m [1H, H1'], 6.21 m [1H, H1'], 6.07 m[1H, H1'], 4.38 m [1H, H3'], 4.10 [m, 4H, H4', H5'] 2.38-2.24 m [4H, H2'], 2.22 [3H, CH3], 2.16 [3H, CH3], 2.14 [3H, CH3]

31P NMR: (Bruker DPX 300) in D2O: 2.14

Mass spectroscopy (ESI-MS) calc 742.66 found [M-H]: 741.73

EXAMPLE 2

Synthesis of a T(P(=NSO2PhNHAc)T9 Oligonucleotide

The oligonucleotide synthesis was carried out on a 1 µmol scale on an ABI 394 synthesizer. Commercially available dT CPG support was used as the solid phase. All chemicals for the standard synthesis were obtained from Glen Research.

In the first synthesis cycle the oxidizer containing iodine was replaced by a 0.1 M solution of p-NAc phenylsulfonyl azide (Sigma Aldrich) in anhydrous acetonitrile. The oxidation time was extended to 16 min. The linkage of the remaining dT phosphoramidites was carried out according to standard protocols.

The product was cleaved from the support for 2 h at room temperature with 33% ammonia and separated by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant was measured at 260 nm. There was a main fraction which contained the desired product. The solvent was removed on a vacuum centrifuge. The residue was taken up in redistilled water and was again evaporated in a vacuum. This procedure was repeated three times. The residue was then dissolved in redistilled water and lyophilized.

Mass spectroscopy (ESI-MS) calc: 3176.25 found [M-H]: 3176.0

EXAMPLE 3

Synthesis of a Fluorescein-Labeled Oligonucleotide

5' AAT ACC TGT ATT CCT CGC CTG TC fluorescein-3' in which each P=O is replaced by P=N-pPh-NAc (SEQ ID NO: 4)

The oligonucleotide synthesis was carried out on a 1 µmol scale on an ABI 394 synthesizer. Commercially available LIGHTCYCLER (Roche Diagnostics GmbH) fluorescein CPG (Roche Applied Science) was used as the support material. All chemicals for the standard synthesis were obtained from Glen Research. Phosphoramidites with tert. butylphenoxy-acetyl protective groups (known as "tac" or "Expedite" monomers) from Proligo were used.

The standard protocol was used for the synthesis, where the oxidizer containing iodine was replaced by a 0.1 M solution of p-NAc phenylsulfonyl azide (Sigma Aldrich) in anhydrous acetonitrile and the oxidation time was extended to 16 min.

The product was cleaved from the support for 2 h at room temperature with 33% ammonia and separated by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant was measured at 260 nm. There was a main fraction which contained the desired product. The solvent was removed on a vacuum centrifuge. The residue was taken up in redistilled water and was again evaporated in a vacuum. This procedure was repeated three times. The residue was then dissolved in redistilled water and lyophilized.

Mass spectroscopy (ESI-MS) calc: 11839 found [M-H]: 11839.9

EXAMPLE 4

Synthesis of Chimeric Oligonucleotides in which P=O was Replaced by P=N-Acc at Specific Positions The syntheses were carried out oh a 1 µmole scale on an ABI 394 synthesizer. In order to not have to change the oxidizer during the synthesis, the synthesis programme was modified such that the N3-Acc solution can be attached at an extra base position. Due to limitations of the programming the azide was reacted together with the activator. This had no effect on the modification. The reaction time of the N3 Acc with the trivalent phosphorus intermediate was 5 min.

All chemicals for the standard synthesis were obtained from Glen Research. Phosphoramidites with tert. butylphenoxy acetyl protective groups (known as "tac" or "Expedite" monomers) from Proligo were used. The purification was carried out as described above.

Support: fluorescein CPG: N3-Acc: p-NAc phenylsulfonyl azide (Sigma Aldrich).

The following probes each with an identical SEQ ID NO: 4 were synthesized and subsequently analysed by mass spectroscopy:

b) Preparation of a Dabsyl Support for Oligonucleotide Synthesis

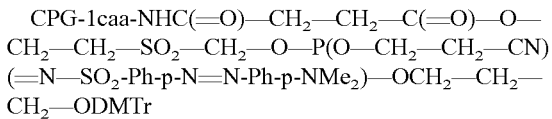

1.2 g phospholink CPG load 49 µmol/g was filled into a Schlenk frit and washed with anhydrous acetonitrile under argon. Then it was washed with 0.1 dichloroacetic acid in methylene chloride until the filtrate is colourless. Subsequently it was thoroughly washed with anhydrous acetonitrile. Afterwards it was washed with 2 ml 0.25 M dicyanoimidazole in acetonitrile (activator) and 2 ml activator and immediately 2 ml 0.1 M solution of the spacer C3 phosphoramidite was added. The suspension was then allowed to stand for 3 min. It was filtered under argon pressure. Then it was washed with 2 ml activator, and again 2 ml activator and immediately 2 ml of a 0.1 M solution of the spacer C3 phosphoramidite were added. Then the preparation was allowed to stand for 12 min. The solvent was removed by filtration under argon pressure, 2 ml of a 0.1 M solution of dabsyl azide in methylene chloride was added and the mixture is allowed to stand for 15 min. The modified CPG was finally washed with 100 ml methylene chloride and then with 100 ml anhydrous acetonitrile and dried in a vacuum.

| Modification (SEQ ID NO: 4) | Mass calculated | Mass found |
| --- | --- | --- |
| 5'-AATACCTGTATTCCTCGCCTGTp1Cfluorescein-3' | 7718 | 7718.6 |
| 5'-Ap1ATACCTGTATTCCTCGCCTGTC fluorescein-3' | 7718 | 7718.9 |
| 5'-AATACCTGp1TATTCGTCp1CCCTGTC-fluorescein-3' | 7915 | 7914.9 |
| 5'-Ap1Ap1Tp1Ap1Cp1Cp1Tp1Gp1Tp1Ap1Tp1TCCTCGCCTGTC-fluorescein-3' | 9681 | 9681.9 |
| 5'-AATACCTGTATTp1Cp1Cp1Tp1Cp1Gp1Cp1Cp1Tp1Gp1Tp1C-fluorescein-3' | 9681 | 9681.8 |
| 5'-Ap1Ap1Tp1ACCTGTATp1Tp1Cp1CTCGCCTp1Gp1Tp1C-fluorescein-3' | 9288 | 9289.8 | p1 is a P = N-pPh-NAc mimetic

EXAMPLE 5

3'-Terminal Labeling According to the Invention a) Preparation of Dabsyl Azide 0.71 g (2.19 mmol) dabsyl chloride was dissolved in 10 ml acetone. A solution of 142 mg (2.19 mmol) sodium azide in 2 ml water was slowly added dropwise while cooling on ice and stirring. It was stirred for 2 h at 0° C. and then stirred for 2 h at room temperature. Then a solution of 32 mg sodium azide (0.5 mmol) in 500 µl water was added and stirred for 1 h at room temperature. (TLC silica gel $CH_2Cl_2$). 200 ml methylene chloride was then added to the suspension and filtered. The filtrate was shaken out twice with water and once with 5% sodium hydrogen carbonate solution and then twice with water. The separated organic phase was dried over sodium sulphate. The solvent was removed by distillation on a rotary evaporator at a bath temperature of <20° C. The residue was suspended in 2 ml acetonitrile and filtered. This residue was washed with ether.

Crude yield 280 mg. The azide is used directly on the DNA synthesizer or to prepare a support without further purification.

c) Oligonucleotide Synthesis Using the Dabsyl Support (SEQ ID NO: 5):

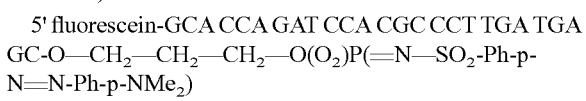

The oligonucleotide synthesis was carried out on a 1 µmole scale on an ABI 394 synthesizer. The dabsyl-CPG from example 5a was used as a support material. 6-Carboxyfluorescein phosphoramidite (Glen Research, Report No. 10 (GR10-1) (1997) 1-12) was used for the 5'-labeling.

All other chemicals for standard synthesis were obtained from Glen Research. As described under 4) phosphoramidites with tert butylphenoxyacetyl protective groups (known as "tac" or "Expedite" monomers) from Proligo were used. The synthesis was carried out according to a standard protocol. The cleavage and purification was also carried out as described in 4.

Mass spectroscopy (ESI-MS) calc: 8973 found [M-H]: 8973.1

EXAMPLE 6

Real Time PCR and Melting Curve Analysis

A quantitative real time PCR of factor V DNA with subsequent melting curve analysis was carried out on a LIGHTCYCLER 1.2 instrument (Roche Diagnostics GmbH) in order to analyse the effect of phosphate mimetics on hybridization. Primers were used in combination with a pair of fluorescein/LIGHTCYCLER Red 640 FRET hybridization probes. The primers and the 5' LIGHTCYCLER Red 640 probe were kept constant. The various 3' fluorescein probes modified on the phosphate from example 4 and the unmodified fluorescein probe as a reference were used as FRET donor probes. The effect on the crossing point which is a measure for the amplification efficiency and the effect on the melting point were evaluated.

20 µl of a PCR reaction mixture was prepared as follows for the amplification of a factor V DNA fragment.

106 copies of a plasmid which contains the factor V wild type gene and mutants (Gene Bank Accession No. M 014335)
13 mM MgCl2
500 nM each primers having the SEQ ID NO: 1 and 2
200 nM each FRET hybridization probes having the SEQ ID NO: 3 and 4

The LIGHTCYCLER DNA Master Hyb Probes Kit (Roche Applied Science, Cat. No. 2158825) was used for all other PCR components according to the manufacturer's instructions.

The following sequences were used as primers and probes:

```
                                       SEQ ID NO: 1
forward primer:
5' GAG AGA CAT CGC CTC TGG GCT A SEQ ID NO: 2
reverse pnmer
5' TGT TAT CAC ACT GGT GCT AA SEQ ID NO: 3
FRET acceptor probe
5' LC-Red 640 AGG GAT CTG CTC TTA CAG ATT AGA AGT

AGT CCT ATT

SEQ ID NO: 4
FRET donor probe
5' AAT ACC TGT ATT CCT CGC CTG TC-fluorescein
```

The following temperature program was used for the amplification on the LIGHTCYCLER 1.2 (Roche Applied Science).

|  | T [° C.] | T [sec] | ramp rate [° C./sec] | acquisition | cycles |
|---|---|---|---|---|---|
| denaturation | 95 | 30 | 20.0 | None | 1 |
| amplification | 95 | 0 | 20.0 | None | |
| | 55 | 10 | 20.0 | Single | 45 |
| | 72 | 10 | 20.0 | None | |

The real time monitoring was carried out over 45 cycles using the 2nd derivative threshold method in which the fluorescence signal was measured in a detection channel that is specific for the LIGHTCYCLER Red 640 emission (at 640 nm) and the arithmetic background correction mode was used to normalize the initial signal.

After the amplification a melting curve analysis was carried out according to the instructions of the LIGHTCYCLER manual (Roche Applied Sciences).

The following temperature program was used:

|  | T [° C.] | t[sec] | ramp rate [° C./sec] | Acquisition | cycles |
|---|---|---|---|---|---|
| melting curve | 95 | 0 | 20.0 | None | |
| | 45 | 60 | 20.0 | Continuous | 1 |
| | 75 | 10 | 0.1 | None | |
| cooling | 40 | 30 | 20.0 | None | 1 |

The absolute fluorescence signals are measured as above in the 640 nm channel and subsequently the first derivative was calculated from this.

The crossing points are shown in the following table as a measure for the amplification efficiency when using different modified donor probes. The table also shows the measured melting temperatures of the various donor probes for the factor V wild type sequence and the factor V mutant sequence.

| Modification (SEQ ID NO: 4) | Cp | Tm wt | Tm mt |
|---|---|---|---|
| 5' AATACCTGTATTCCTCGCCTGTC-fluorescein-3' (ref) | 22.11 | 64.92 | 56.98 |
| 5' AATACCTGTATTCCTCGCCTGTp1C fluorescein-3' | 22.61 | 64.32 | 56.26 |
| 5' Ap1ATACCTGTATTCCTCGCCTGTC fluorescein-3' | 22.51 | 64.80 | 56.80 |
| 5' AATACCTGp1TATTCCTCp1GCCTGTC-fluorescein-3' | 22.26 | 64.28 | 55.89 |
| 5' Ap1Ap1Tp1Ap1Cp1Cp1Tp1Gp1Tp1Ap1Tp1TCCTCGCCT GTC-fluorescein-3' | 21.40 | 60.69 | 52.19 |
| 5' AATACCTGTATTp1Cp1Cp1Tp1Cp1Gp1Cp1Cp1Tp1Gp1Tp1C-fluorescein-3' | 21.91 | 60.74 | 52.14 |

-continued

| Modification (SEQ ID NO: 4) | Cp | Tm wt | Tm mt |
|---|---|---|---|
| 5' Ap1Ap1Tp1ACCTGTATp1Tp1Cp1CTCGCCTp1Gp1Tp1C-fluorescein-3' | 22.00 | 61.40 | 52.83 | p1 is a P = N-pPh-NAc mimetic

As shown in the table the crossing point is not significantly effected by introducing the modifications according to the invention, i.e., the PCR efficiency is unchanged.

Moreover, no effect is found on the measured melting temperature in the case of the once or two-fold modified probes. Furthermore, multiply modified probes only exhibit a moderate change in the melting point of no more than 4° C. whereas the ability for mismatch discrimination is retained.

EXAMPLE 7

Real Time PCR+Melting Curve Analysis a) Preparation of Lissamine Azide (=RhodamineB)

A solution of 195 mg (3.0 mmol) sodium azide in 5 ml water was added dropwise at 0° C. to a solution of 577 mg (1 mmol) sulforhodamine B acid chloride in 20 ml acetone. The mixture was stirred for 2 h at 0° C. and then for 6 h at room temperature. The mixture was transferred to a separating funnel and 300 ml water and 300 ml methylene chloride were added. The organic phase was separated and washed twice with 100 ml water. The organic phase was dried over sodium sulfate. The solvent was removed by distillation on a rotary evaporator. The residue (140 mg) was used without further purification for oligonucleotide synthesis.

b) Synthesis of a SEQ ID NO:3 FRET Acceptor Probe

```
Ap*GG GAT CTG CTC TTA CAG ATT AGA AGT AGT CCT ATT-p p* = P = NS(O)2-rhodamine-B
```

The oligonucleotide synthesis was carried out on a 1 μmole scale on an ABI 394 synthesizer. Commercially available phospholink CPG (Glen Research) was used as the support material. All chemicals for the standard synthesis were obtained from Glen Research. Phosphoramidites with tert. butylphenoxyacetyl protective groups (known as "tac" or "Expedite" monomers) from Proligo were used.

The standard protocol (trityl off) was used for the synthesis in which the oxidizer in the last cycle was replaced by a 0.1 M solution of lissamine azide in anhydrous acetonitrile and the oxidation time was extended to 16 min.

The product was cleaved from the support for 2 h at room temperature with 33% ammonia and separated by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The LTV absorption of the eluant is measured at 260 nm. There was a main fraction which contained the desired product. The solvent was removed on a vacuum centrifuge. The residue was taken up in redistilled water and was again evaporated in a vacuum. This procedure was repeated three times. The residue was then dissolved in redistilled water and lyophilized. Mass spectroscopy (ESI-MS) calc: 11710 found [M-H]: 11710.5.

c) Real Time PCR

In order to demonstrate the suitability in real time PCR a real time PCR of factor V DNA was carried out on a LIGHT-CYCLER 2.0. Primers were used in combination with a pair of fluorescein/lissamine FRET hybridization probes where Lissamine (rhodamineB) acted as a FRET acceptor. Quantification curves were recorded and the cp value was determined as a function of the concentration of the target nucleic acid.

A teal time PCR and melting curve analysis were carried out according to example 6 for the amplification of $10^4$ and $10^6$ copies of a factor V DNA fragment. A fluorescein donor probe according to example 6 (SEQ ID NO: 4) which was not further modified and a FRET acceptor probe according to example 7b (SEQ ID NO: 3) were used for this.

| | T [° C.] | T [sec] | ramp rate [° C./sec] | acquisition | cycles |
|---|---|---|---|---|---|
| denaturation | 95 | 30 | 20.0 | None | 1 |
| amplification | 95 | 0 | 20.0 | None | |
| | 55 | 10 | 20.0 | Single | 45 |
| | 72 | 10 | 20.0 | None | |

-continued

| | T [° C.] | T [sec] | ramp rate [° C./sec] | acquisition | cycles |
|---|---|---|---|---|---|

The fluorescence signal was measured in the 610 nm detection channel. The 610/530 background correction mode was used to normalize the raw signal. A cp value of 22 was determined for $10^6$ copies and a cp of 26 was determined for $10^4$ copies.

The melting point for the wild type was determined as 64.69° C. and 56.24° C. was determined as the melting point for the mutant ($10^6$ copies).

EXAMPLE 8

Real Time PCR with Modified Primers

A quantitative real time PCR of human Factor V DNA was carried out on a LIGHTCYCLER 1.2 instrument (Roche Diagnostics GmbH) in order to analyse the effect of phosphate mimetics on primer elongation. The P=N-pPh-NAc mimetic which was introduced at different positions of a primer pair used for amplification of human Factor V DNA. The modified primers were, synthesized according to example 4. Purification was done by the Reversed Phase chromatography of example 3 in the Trityl on mode. Detritylation was performed by treating with 80% acetic acid for 20 min.

This primers were used in combination with a pair of fluorescein/LIGHTCYCLER Red 640 FRET hybridization probes according to example 6. The Fluorescein probe and the 5' LIGHTCYCLER Red 640 probe (SEQ ID NO: 3 and 4) were kept constant. Various combinations of modified and unmodified primers were tested. As reference unmodified primers were used. The effect on the crossing point which is a measure for the amplification efficiency was evaluated.

The real time monitoring was carried out over 45 cycles using the 2nd derivative threshold method in which, the fluorescence signal was measured in a detection channel that is specific for the LIGHTCYCLER Red 640 emission (at 640 nm) and the arithmetic background correction mode was used to normalize the initial signal.

The absolute fluorescence signals are measured as above in the 640 nm channel and subsequently the first derivative was calculated from this. The crossing points are shown in the following table as a measure for the amplification efficiency when using different modified primers.

```
Primer combinations
SEQ ID NO: 1
SEQ ID NO: 2                              Cp

5' GAG AGA CAT CGC CTC TGG GCT A         20.36
5' TGT TAT CAC ACT GGT GCT AA

5' GAG AGA CAT CGC CTC TGG GCTA          22.08
5' TGT TAT CAC ACT GGT GCT Ap1A

5' GAG AGA CAT CGC CTC TGG GCT A         22.50
5' TGT TAT CAC ACT GGT Gp1CT AA

5' GAG AGA CAT CGC CTC TGG GCT A         21.36
5' TGT TAT CAC ACT p1GGT GCT AA

5' GAG AGA CAT CGC CTC TGG GCT p1A       20.80
5' TGT TAT CAC ACT GGT GCT AA

5' GAG AGA CAT CGC CTC TGG p1GCT A       20.85
5' TGT TAT CAC ACT GGT GCT AA

5' GAG AGA CAT CGC CTp1C TGG GCT A       20.61
5' TGT TAT CAC ACT GGT GCT AA

5' GAG AGA CAT CGC CTC TGG GCT p1A       21.76
5' TGT TAT CAC ACT GGT GCT Ap1A

5' GAG AGA CAT CGC CTp1C TGG p1GCT A     22.75
T' TGT TAT CAC ACT GGT Gp1CT AA

5' GAG AGA CAT CGC CTp1C TGG GCT A       21.36
5' TGT TAT CAC ACT p1GGT GCT AA p1 is a P = N-pPh-NAc mimetic
```

As shown in the table, the crossing point is not significantly affected by introducing modifications according to the invention in the primers which shows that the PCR efficiency is nearly unchanged.

EXAMPLE 9

Synthesis of a Fluorescein Labeled Oligonucleotide Comprising a Pyridinium Phosphatmimetikum Synthesis of an oligonucleotide according to SEQ ID NO: 4 was carried out on a 1 μmol scale on an ABI 394 synthesizer. Commercially available LIGHTCYCLER fluorescein CPG (Roche Applied Science) was used as the support material. All chemicals for the standard synthesis were obtained from Glen Research. Phosphoramidites with tort butylphenoxy-acetyl protective groups (known as "tac" or "Expedite" monomers) from Proligo were used.

The protocol from Example 4 was used for the synthesis, whereas during the second cycle as oxidizer a 0.1 M solution of 1,2,6 trimethyl pyridinium 4-azid (RareChem AQ N6 1054) in anhydrous acetonitrile was used and the oxidation time was extended to 16 min. This resulted in an intermediate comprising the structure:

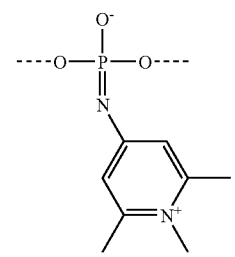

The product was cleaved from the support for 2 h at room temperature with 33% ammonia and separated by reversed phase chromatography on a Poros Oligo R3 4.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant was measured at 260 nm. There was a main fraction which contained the desired product. The solvent was removed on a vacuum centrifuge. The residue was taken up in redistilled water and was again evaporated in a vacuum. This procedure was repeated three times. The residue was then dissolved in redistilled water and lyophilized.

Mass spectroscopy (Maldi-MS Applied Biosystems Voyager System 6327) calc: 7641.32 found [M-H]: 7639.59

EXAMPLE 10

Stability of a dA(P(=NSO2PhNHAc)dT Dinucleotide in Comparison to an Unmodified dAdT at Different Temperatures and pH dA(P(=NSO2PhNHAc)dT was synthesized and purified according to example 1) dAdT was also synthesized according to example 1, but standard oxidizers were used (0.02 M iodine in THF).

The dimers were exposed for different times and temperatures in 10 mM Tris buffer at different pH values 7.0, 8.0, and 9.0. Samples were left at room temperature (approx. 24° C.) for 24 h or at 95° C. for 60 min respectively 16 h. 150 μL aliquots were removed before and after the experiment and 100 μL volumes were injected on the HPLC.

The decomposition was monitored by reverse phase HPLC on an analytical X-Bridge column (2.5 μm, 4.6×50 mm i.d.) with a Waters 2690 separation module. Detection was carried out with a Waters 2996 PAD Detector (260 nm). A mobile phase of 0.1 M triethylammonium acetate (pH 6.8) pumped with a 95% gradient of acetonitrile at flow rate of 1.0 ml/min was used. The destruction rate of the dimers was judged by monitoring the retention time rt of the dimer signal (Software Millenium, Waters) and determining whether additional peaks with retention times different than that, of the nucleotide dimer occur. Results are shown in the following table:

|  | dAdT | dA(P(=NSO2PhNHAc)dT |
|---|---|---|
| pH 7.0 | | |
| Starting solution | rtHPLC = 2.39 | rtHPLC = 2.93 |
| 24 h at rt (24° C.) | rtHPLC = 2.39 | rtHPLC = 2.93 |
| 1 h at 95° C. (dry oven) | rtHPLC = 2.48 | rtHPLC = 2.99 |
| 16 h at 95° C. (dry oven) | rtHPLC = 2.42<br>1 new peak t = 6.2 | rtHPLC = 2.99<br>2 new peaks t = 1.2, 2.0. |

-continued

|  | dAdT | dA(P(=NSO2PhNHAc)dT |
|---|---|---|
| pH 8.0 | | |
| Starting solution | rtHPLC = 2.38 | rtHPLC = 2.96 |
| 24 h at rt (24° C.) | rtHPLC = 2.38 | rtHPLC = 2.96 |
| 1 h at 95° C. (dry oven) | rtHPLC = 2.42 | rtHPLC = 2.92 |
| 16 h at 95° C. (dry oven) | rtHPLC = 2.41<br>1 new peak 6.2 | rtHPLC = 2.92 |
| pH 9.0 | | |
| Starting solution | rtHPLC = 2.41 | rtHPLC = 2.92 |
| 24 h at rt (24° C.) | rtHPLC = 2.41 | rtHPLC = 2.92 |
| 1 h at 95° C. (dry oven) | rtHPLC = 2.42 | rtHPLC = 2.95 |
| 16 h at 95° C. (dry oven) | rtHPLC = 2.43 | rtHPLC = 2.95 |

There unmodified dimer was stable at pH 7.0, 8.0 and 9.0 for 24 h at rt, for 1 h at 95° C. and started decomposing after 16 h at pH 7.0 and pH 8.0. The modified dimer was stable at, pH 7.0, 8.0 and 9.0 for 24 h a rt, for 1 h at 95° C. and started decomposing after 16 h at 95° C. at pH 7.0.

What is claimed is:

1. A chemical compound comprising at least once the structure

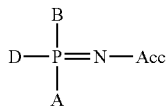

wherein

A represents the 5' end of a nucleotide, a nucleotide chain, or a linker bound to a solid phase, B represents the 3' end of a nucleotide, a nucleotide chain, or a linker, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and chinolinium.

2. The compound of claim 1 wherein R or R' alone or in combination with the electron acceptor contain a detectable unit or a functional group.

3. The compound of claim 1 wherein A and B together comprise at least two nucleotide residues.

4. A process for producing a modified oligonucleotide comprising the steps of providing a trivalent phosphorus derivative having a structure

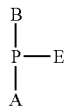

wherein E represents a methyl group or a protected hydroxyl group, A represents a 5' end of a nucleotide, a nucleotide chain, or a linker bound to a solid phase, and B represents a 3' end of a nucleotide, or a nucleotide chain, or a linker, reacting the trivalent phosphorus derivative with an azide having the structure

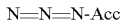

wherein Acc is an electron acceptor or an electron acceptor substituted with a residue R wherein R is an organic substituent and Acc is selected from the group consisting of CN, SO$_2$—R', in which R' contains at least one amino-substituted alkyl, an optionally substituted aryl or an optionally substituted heterocycle, and a six membered N$^+$ heterocycle with at least one alkylated N-atom in ortho- or para-position, said heterocycle being selected from the group consisting of pyridinium, pyrimidinium and chinolinium, under conditions whereby said modified oligonucleotide is formed.

5. The process of claim 4 wherein R or R' is a detectable unit or a functional group.

6. A process for producing a modified oligonucleotide comprising the steps of reacting a 3' phosphoramidite with the 5' OH end of a nascent oligonucleotide chain to produce a trivalent phosphorus derivative and then reacting the trivalent phosphorus derivative with an azide having the structure

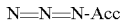

in which Acc is an electron acceptor or an electron acceptor substituted with a residue R and R is any organic substituent, and Acc is selected from a group consisting of CN, SO$_2$—R', in which R' contains at least one amino-substituted alkyl, an optionally substituted aryl or an optionally substituted heterocycle, and a six membered N+ heterocycle with at least one alkylated N-atom in ortho- or para-position, said heterocycle being selected from a group consisting of pyridinium, pyrimidinium and chinolinium, under conditions whereby said modified oligonucleotide is formed.

7. The process of claim 6 wherein R or R' is a detectable unit or a functional group.

* * * * *

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
gagagacatc gcctctgggc ta                                              22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tgttatcaca ctggtgctaa                                                 20

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agggatctgc tcttacagat tagaagtagt cctatt                               36

<210> SEQ ID NO 4
<211> LENGTH: 23

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
aatacctgta ttcctcgcct gtc                                            23

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      oliognucleotide

<400> SEQUENCE: 5
gcaccagatc cacgcccttg atgagc                                         26
```